(12) United States Patent
Audonnet et al.

(10) Patent No.: US 7,294,338 B2
(45) Date of Patent: *Nov. 13, 2007

(54) POLYNUCLEOTIDE VACCINE FORMULA AGAINST CANINE PATHOLOGIES, IN PARTICULAR RESPIRATORY AND DIGESTIVE PATHOLOGIES

(75) Inventors: Jean-Christophe Audonnet, Lyons (FR); Annabelle Bouchardon, Lyons (FR); Michel Riviere, Ecully (FR)

(73) Assignee: Merial, Lyon (FR)

( * ) Notice: Subject to any disclaimer, the term of this patent is extended or adjusted under 35 U.S.C. 154(b) by 168 days.

This patent is subject to a terminal disclaimer.

(21) Appl. No.: 10/211,502

(22) Filed: Aug. 2, 2002

(65) Prior Publication Data

US 2003/0133947 A1   Jul. 17, 2003

Related U.S. Application Data

(60) Continuation-in-part of application No. 09/784,982, filed on Feb. 16, 2001, now Pat. No. 6,586,412, which is a division of application No. 09/232,477, filed on Jan. 15, 1999, now Pat. No. 6,228,846, which is a continuation-in-part of application No. PCT/FR97/01316, filed on Jul. 15, 1997.

(51) Int. Cl.
*A61K 39/12* (2006.01)
(52) U.S. Cl. ............... 424/199.1; 435/320.1; 514/44
(58) Field of Classification Search ............ 424/184.1, 424/204.1, 224.1, 818; 435/41, 91.4, 320.1
See application file for complete search history.

(56) References Cited

U.S. PATENT DOCUMENTS

| | | | | |
|---|---|---|---|---|
| 5,494,807 A | * | 2/1996 | Paoletti et al. | ............. 435/69.3 |
| 5,843,456 A | * | 12/1998 | Paoletti et al. | ............ 424/199.1 |
| 5,846,946 A | | 12/1998 | Huebner et al. | |
| 6,063,385 A | | 5/2000 | Schultz | |
| 6,187,759 B1 | | 2/2001 | Tarpey et al. | |
| 6,228,846 B1 | * | 5/2001 | Audonnet et al. | ............. 514/44 |
| 6,451,770 B1 | * | 9/2002 | Rijsewijk et al. | ............. 514/44 |
| 6,586,412 B2 | * | 7/2003 | Audonnet et al. | ............. 514/44 |

FOREIGN PATENT DOCUMENTS

| | | |
|---|---|---|
| WO | WO 95/20660 | 8/1995 |
| WO | WO 97/40163 | 10/1997 |
| WO | WO 97/41236 | 11/1997 |

OTHER PUBLICATIONS

Endres et al. Suppression of simian immunodeficiency virus replication by human immunodeficiency virus type 1 trans-dominant negative rev mutants. Journal of Virology, Aug. 1995, vol. 69(8), p. 5164-5166.*
Xiang et al. Immune responses to nucleic acid vaccines to rabies virus. Virology, 1995, 209, p. 569-579.*
Ertl et al. Plasmid vectors as anti-viral vaccines. DNA Vaccines, A new Era in Vaccinology, 1995, vol. 6, p. 77-87.*
Perrin et al. Immunization of dogs with a DNA vaccine induces protection against rabies virus. Vaccine, 2000, vol. 18, 479-486.*
Gurunathan et al. DNA vaccines: immunology, application, and optimization. Annu. Rev. Immunol., 2000, vol. 18, 927-974.*
Z.Q. Xiang, et al., "Immune Response to Nucleic Acid Vaccines to Rabies Virus", Virology, vol. 209-2 (1995) pp. 569-579.
Jiang et al., Nucleic Acid Immunization Protects Dogs Against Challenge with Virulent Canine Parvorirus, Vaccine 16(6):601-607, 1998.
Sixt et al., Canine Distemper Virus DNA Vaccination Induces Humoral and Cellular Immunity and Protects Against a Lethal Intracerebral Challenge, Journal of Virology, 72(11):8472-8476, 1998.
Tighe et al., Gene Vaccination: Plasmid DNA is More Than Just a Blueprint. Immunology Today 19(2):89-97, 1998.
Ertl, H.C. et al., "Plasmid Vectors as Anti-Viral Vaccines" DNA Vaccines, A new Era in Vaccinology 1995, vol. 6: 77-87.
Prrin, P., et al., "Immunization of Dogs with a DNA Vaccines Induces Protection Against Rabies Virus" Vaccine 2000, vol. 18: 479-486.
Osorio, J.E., et al. "Immunization of Dogs and Cats with a DNA Vaccine Against Rabies Virus" Vaccine 1999, vol. 17: 1109-1116.
Schultz, J. et al. "Update on antiviral DNA vaccine research (1998-2000)." Intervirology 2000 43:197-217.

* cited by examiner

*Primary Examiner*—Bruce Campell
*Assistant Examiner*—Emily M. Le
(74) *Attorney, Agent, or Firm*—Thomas J. Kowalski; Judy Jarecki-Black; Frommer Lawrence & Haug LLP

(57) ABSTRACT

Disclosed is an immunological or vaccine composition that includes at least one plasmid that contains and expresses in vivo in host canine cells a nucleic acid molecule that encodes an antigen of a canine pathogen, such as rabies G. The plasmid can include more that one nucleic acid molecule such that the plasmid can express more than one antigen. Also disclosed are methods for using and kits employing such compositions.

15 Claims, 10 Drawing Sheets

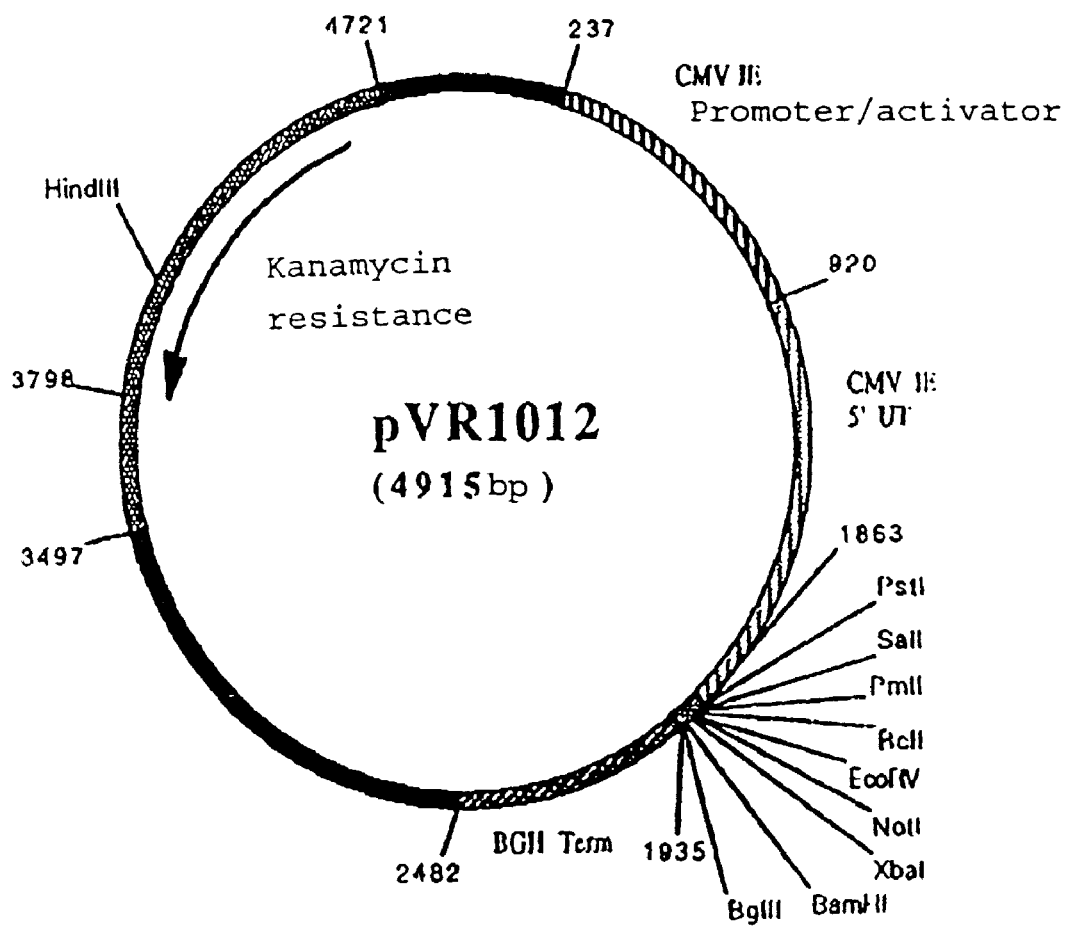
Figure No. 1

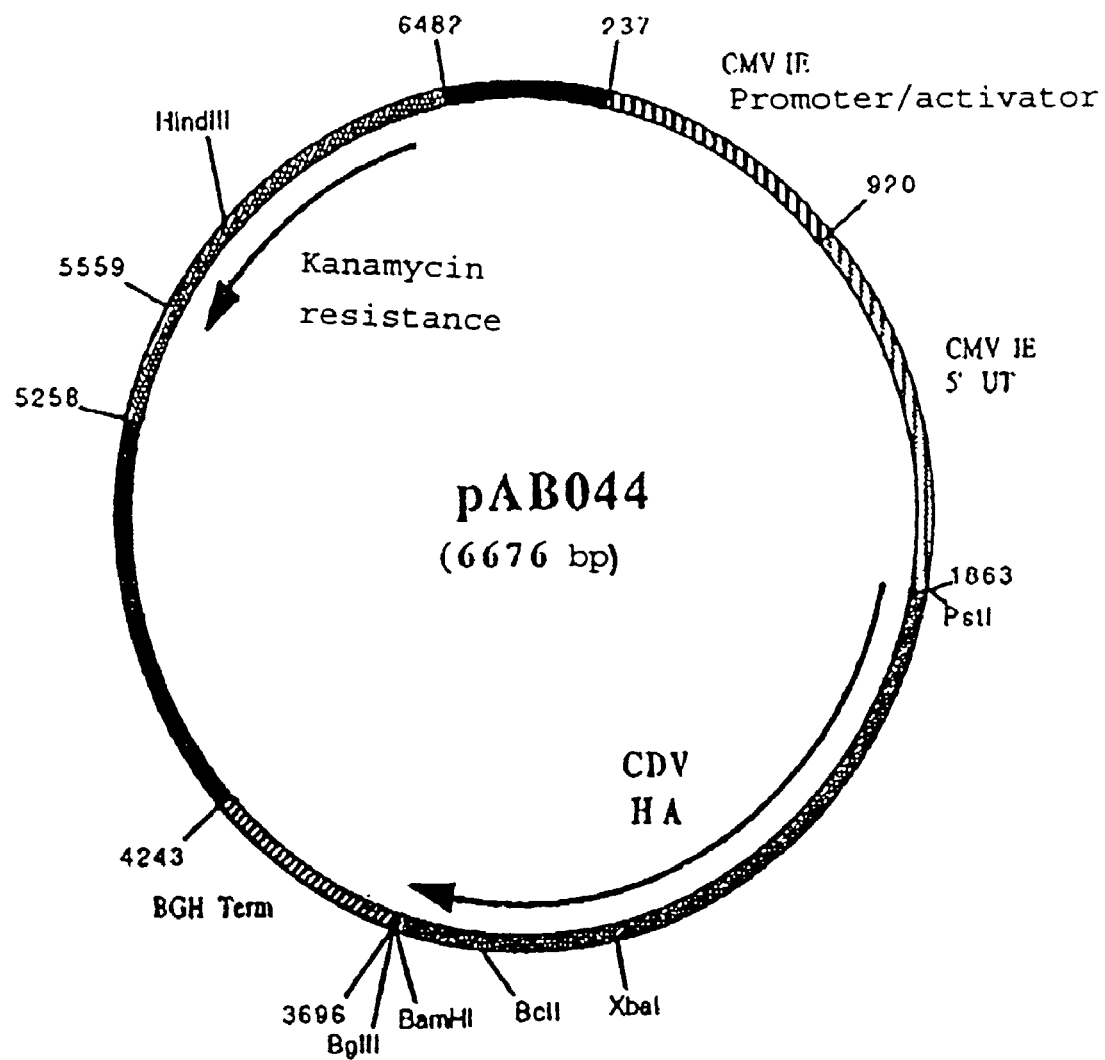
Figure No. 2

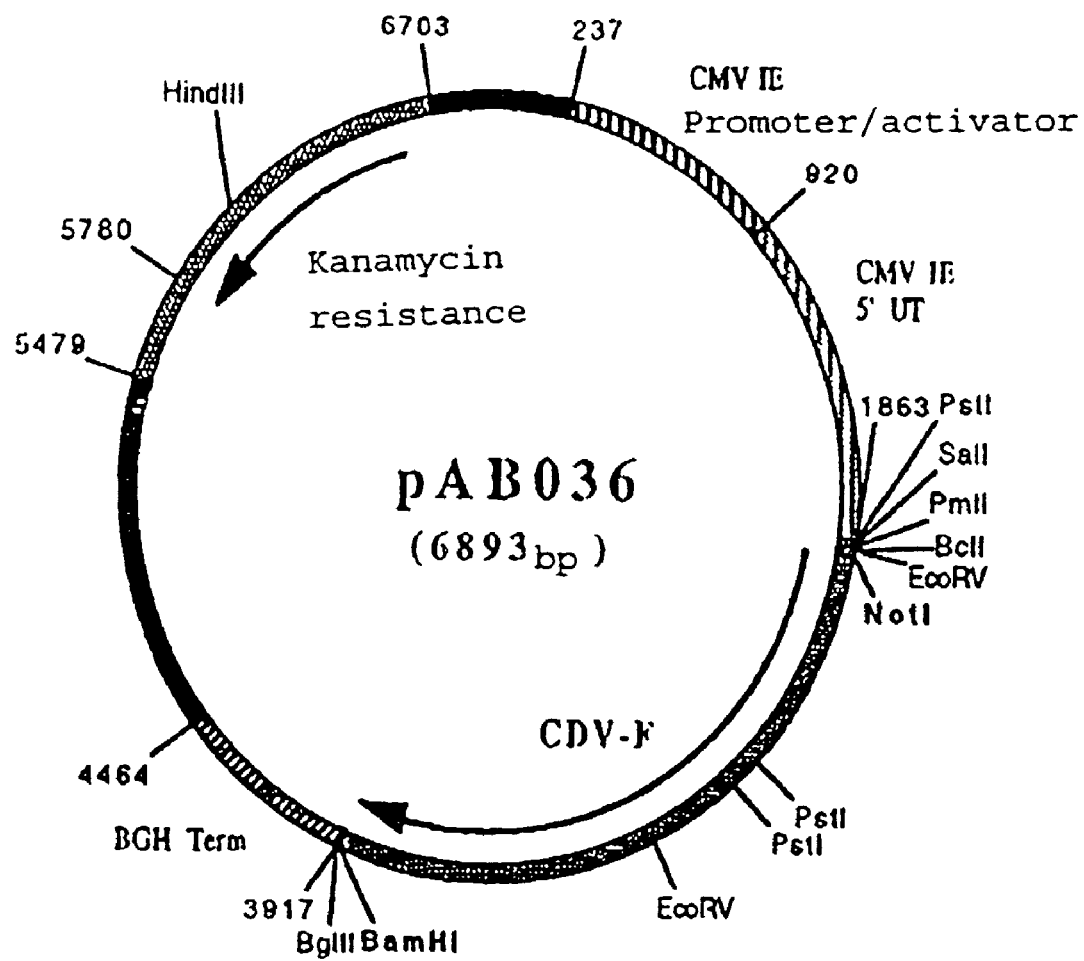
Figure No. 3

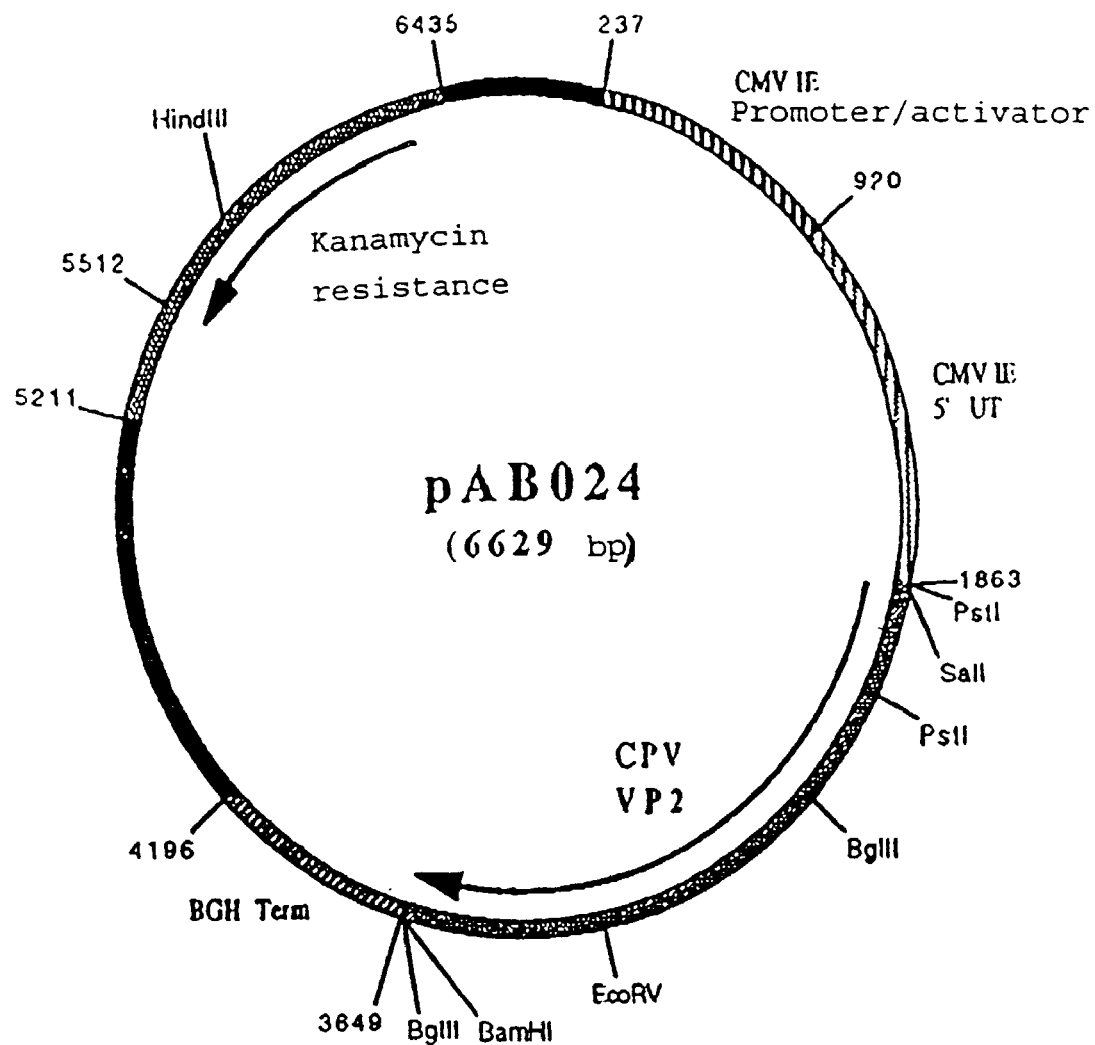
Figure No. 4

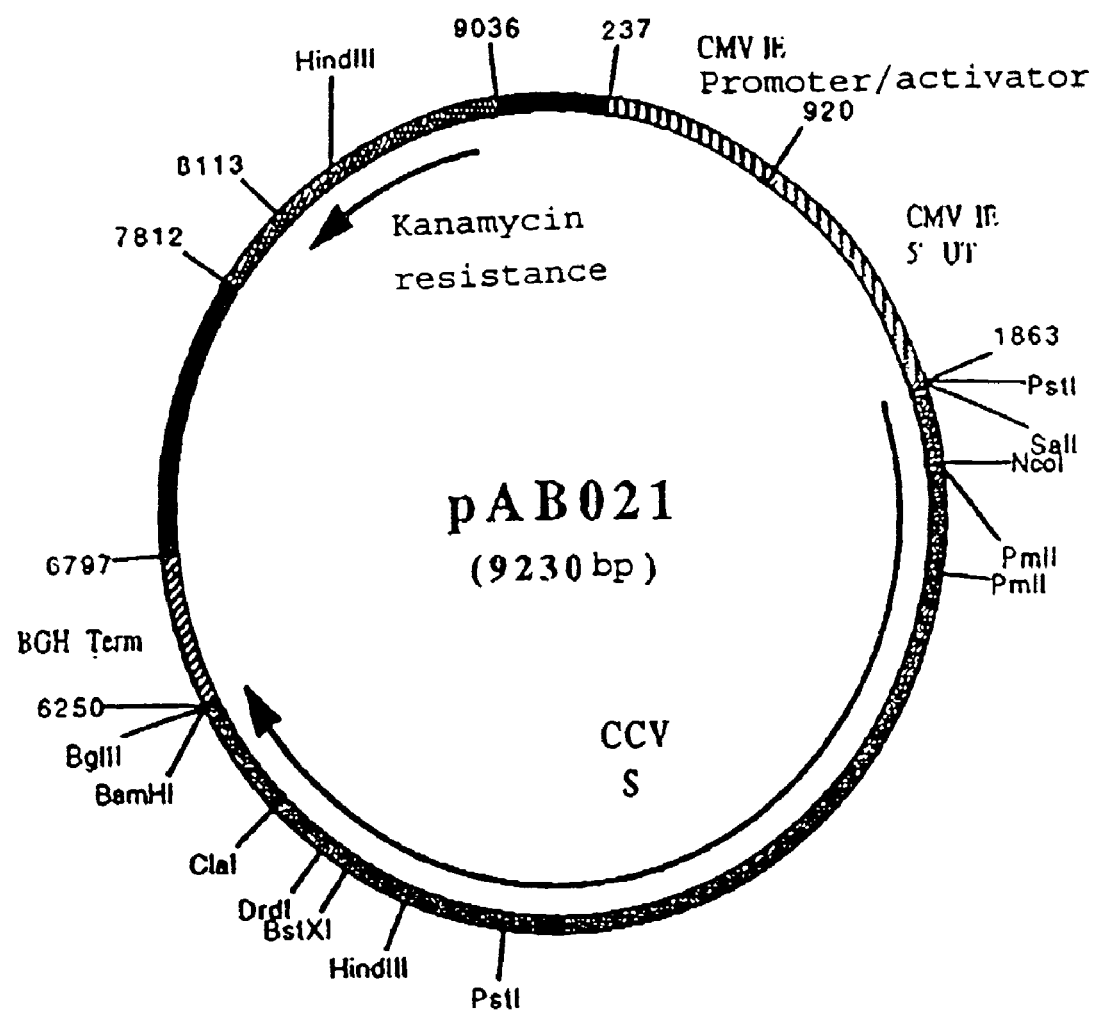
Figure No. 5

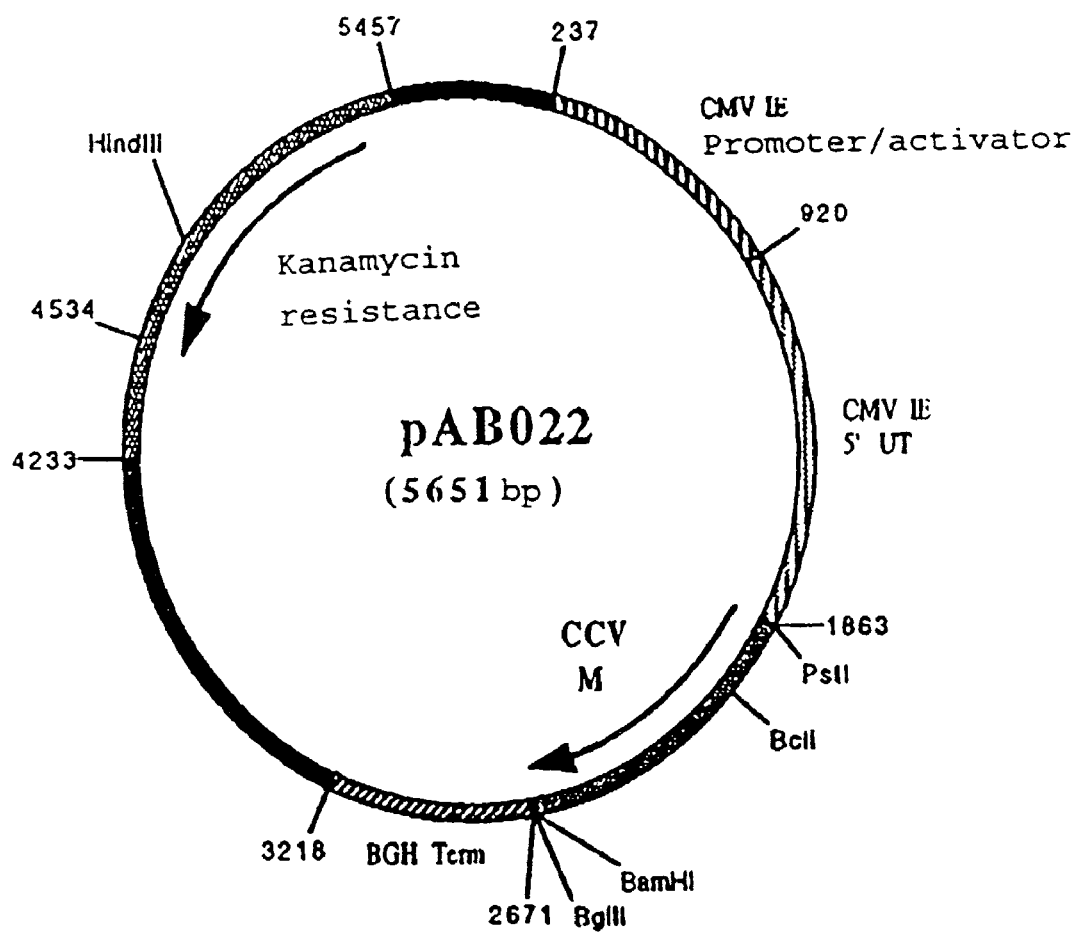
Figure No. 6

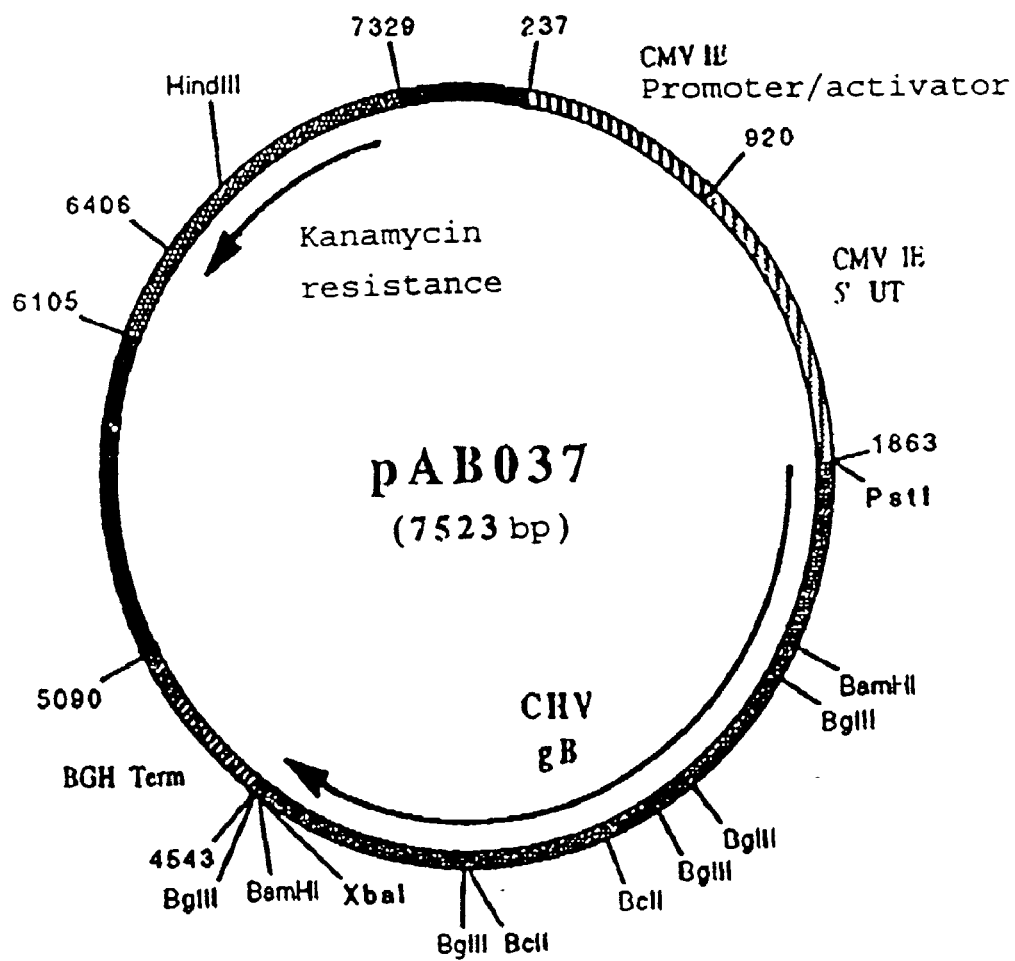
Figure No. 7

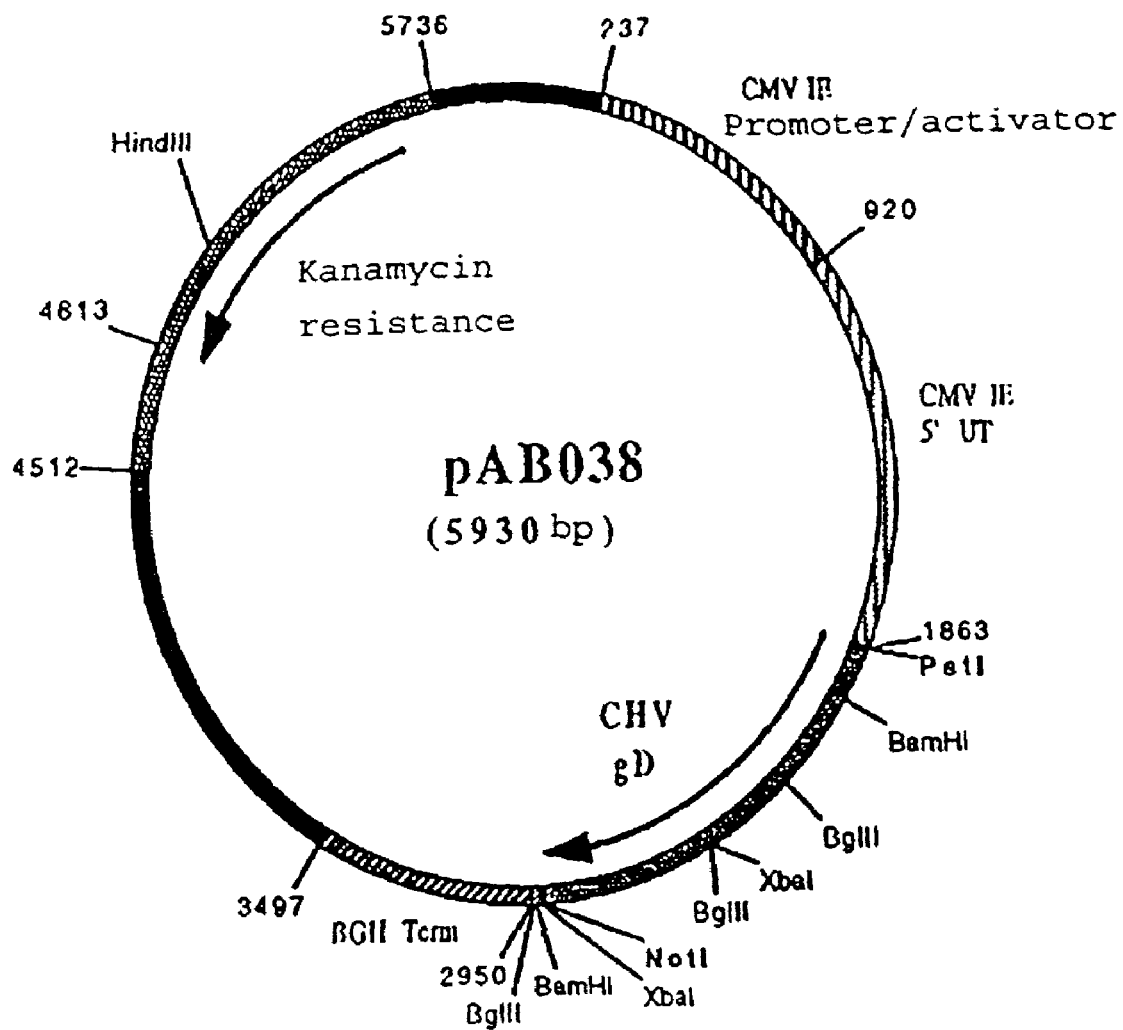
Figure No. 8

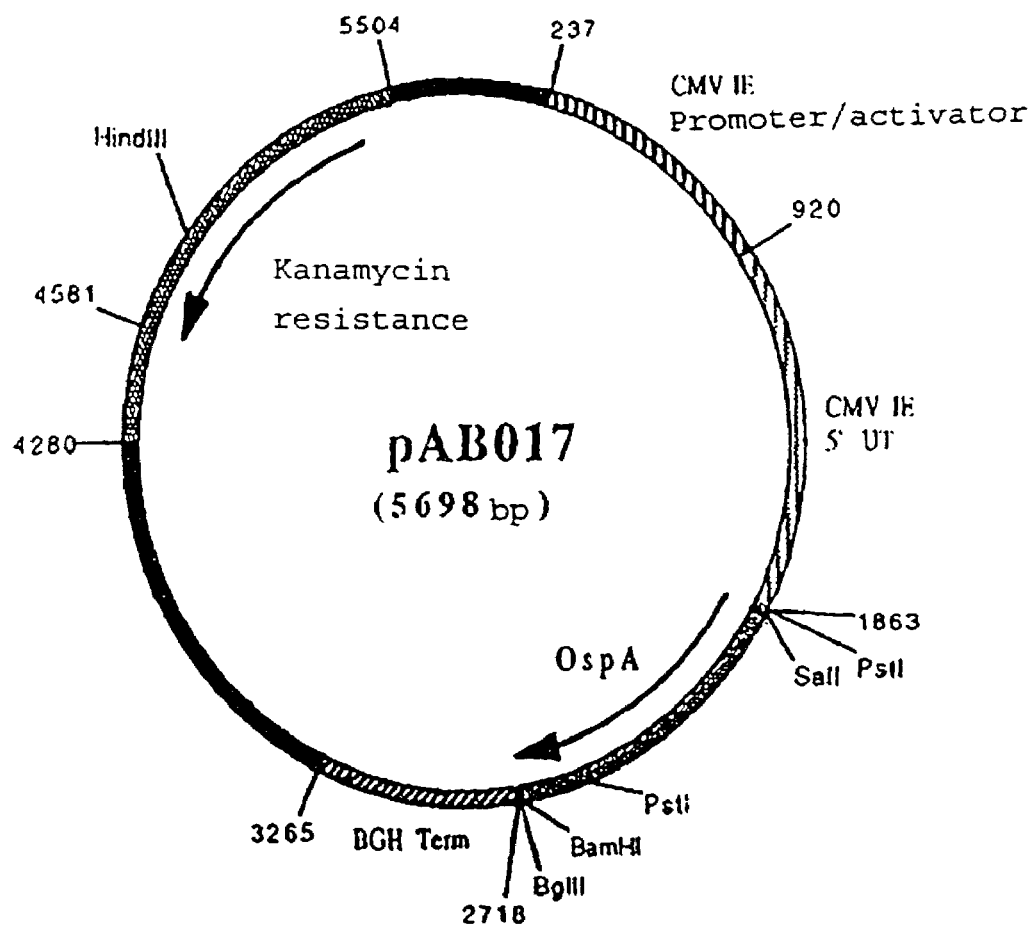
Figure No. 3

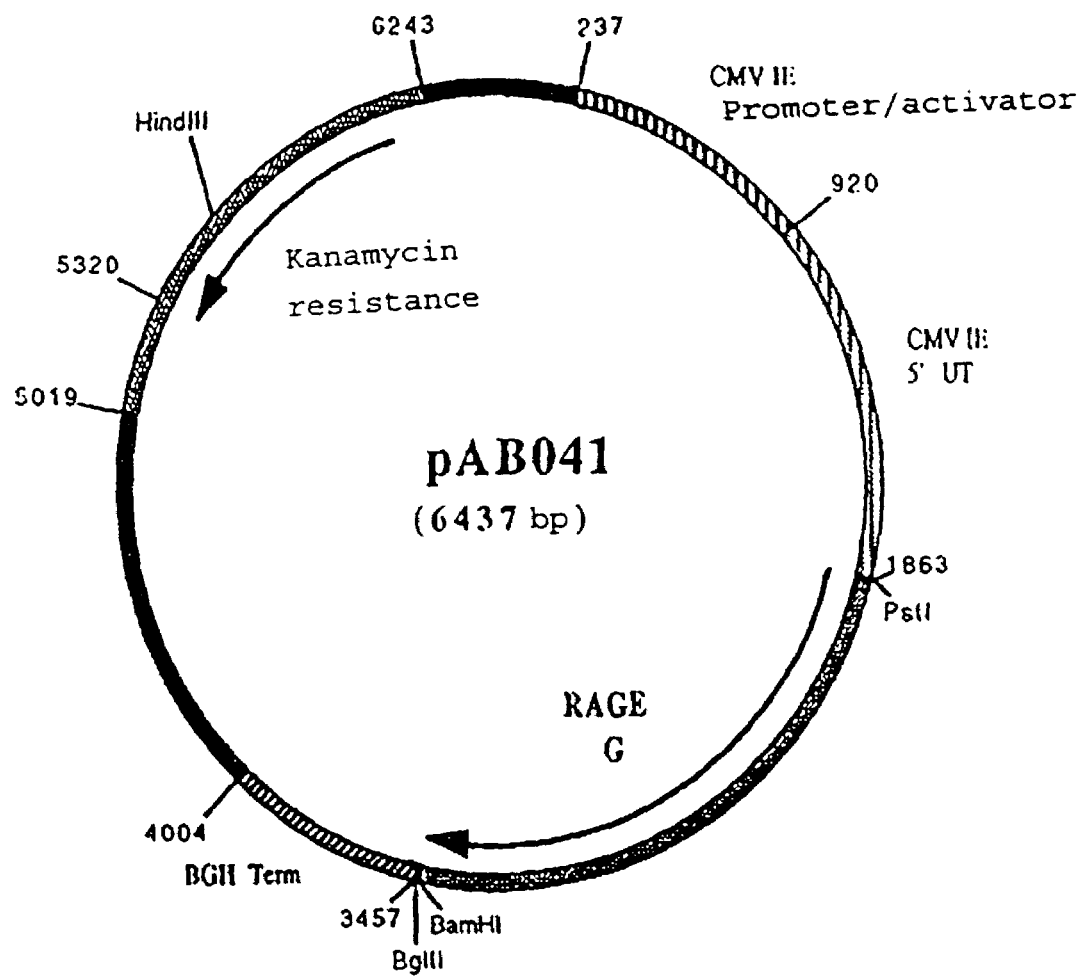
Figure No. 10

SEQUENCE LISTING

<160> NUMBER OF SEQ ID NOS: 18

<210> SEQ ID NO 1
<211> LENGTH: 35
<212> TYPE: DNA
<213> ORGANISM: Borrelia burgdorferi

<400> SEQUENCE: 1
aaaactgcag aatgctcccc taccaagaca aggtg                35

<210> SEQ ID NO 2
<211> LENGTH: 37
<212> TYPE: DNA
<213> ORGANISM: Borrelia burgdorferi

<400> SEQUENCE: 2
cgcggatcct taacggttac atgagaatct tatacgg              37

<210> SEQ ID NO 3
<211> LENGTH: 40
<212> TYPE: DNA
<213> ORGANISM: Borrelia burgdorferi

<400> SEQUENCE: 3
ataagaagcg gccgcacatg cacaagggaa tccccaaaag           40

<210> SEQ ID NO 4
<211> LENGTH: 32
<212> TYPE: DNA
<213> ORGANISM: Borrelia burgdorferi

<400> SEQUENCE: 4
cgcggatcca cttcagtgtg atctcacata gg                   32

<210> SEQ ID NO 5
<211> LENGTH: 33
<212> TYPE: DNA
<213> ORGANISM: Borrelia burgdorferi

<400> SEQUENCE: 5
acgcgtcgac atgagtgatg gagcagttca acc                  33

<210> SEQ ID NO 6
<211> LENGTH: 33
<212> TYPE: DNA
<213> ORGANISM: Borrelia burgdorferi

<400> SEQUENCE: 6
cgcggatcct taatataatt ttctaggtgc tag                  33

<210> SEQ ID NO 7
<211> LENGTH: 32
<212> TYPE: DNA
<213> ORGANISM: Borrelia burgdorferi

<400> SEQUENCE: 7
acgcgtcgac atgattgtgc ttacattgtg cc                   32

<210> SEQ ID NO 8
<211> LENGTH: 35
<212> TYPE: DNA
<213> ORGANISM: Borrelia burgdorferi

```
<400> SEQUENCE: 8
cgcggatcct cagtgaacat gaactttttc aatag                          35

<210> SEQ ID NO 9
<211> LENGTH: 34
<212> TYPE: DNA
<213> ORGANISM: Borrelia burgdorferi

<400> SEQUENCE: 9
aaaactgcag aaatgaagaa aattttgttt ttac                           34

<210> SEQ ID NO 10
<211> LENGTH: 33
<212> TYPE: DNA
<213> ORGANISM: Borrelia burgdorferi

<400> SEQUENCE: 10
cgcggatcct tataccatat gtaataattt ttc                            33

<210> SEQ ID NO 11
<211> LENGTH: 34
<212> TYPE: DNA
<213> ORGANISM: Borrelia burgdorferi

<400> SEQUENCE: 11
aaaactgcag aagtatgttt tcattgtatc tata                           34

<210> SEQ ID NO 12
<211> LENGTH: 34
<212> TYPE: DNA
<213> ORGANISM: Borrelia burgdorferi

<400> SEQUENCE: 12
ctagtctaga ttattaaact ttactttcat tttc                           34

<210> SEQ ID NO 13
<211> LENGTH: 34
<212> TYPE: DNA
<213> ORGANISM: Borrelia burgdorferi

<400> SEQUENCE: 13
aaaactgcag aaaatgatta aacttctarr ratc                           34

<210> SEQ ID NO 14
<211> LENGTH: 35
<212> TYPE: DNA
<213> ORGANISM: Borrelia burgdorferi

<400> SEQUENCE: 14
ataagaatgc ggccgcaaag gctaaacatt tgttg                          35

<210> SEQ ID NO 15
<211> LENGTH: 37
<212> TYPE: DNA
<213> ORGANISM: Borrelia burgdorferi

<400> SEQUENCE: 15
acgcgtcgac tatgaaaaaa tatttattgg gaatagg                        37

<210> SEQ ID NO 16
<211> LENGTH: 34
<212> TYPE: DNA
```

-continued

```
<213> ORGANISM: Borrelia burgdorferi

<400> SEQUENCE: 16
cgcggatccc ttattttaaa gcgttttttaa tttc                              34

<210> SEQ ID NO 17
<211> LENGTH: 33
<212> TYPE: DNA
<213> ORGANISM: Borrelia burgdorferi

<400> SEQUENCE: 17
aaaactgcag agatggttcc tcaggctctc ctg                               33

<210> SEQ ID NO 18
<211> LENGTH: 34
<212> TYPE: DNA
<213> ORGANISM: Borrelia burgdorferi

<400> SEQUENCE: 18
cgcggatcct cacagtctgg tctcaccccc actc                              34
```

US 7,294,338 B2

POLYNUCLEOTIDE VACCINE FORMULA AGAINST CANINE PATHOLOGIES, IN PARTICULAR RESPIRATORY AND DIGESTIVE PATHOLOGIES

REFERENCE TO RELATED APPLICATIONS

This application is a Continuation-in-Part of application Ser. No. 09/784,982, filed Feb. 16, 2001, now U.S. Pat. No. 6,586,412, issued Jul. 1, 2003, which is a Divisional of application Ser. No. 09/232,477, filed Jan. 15, 1999, now U.S. Pat. No. 6,228,846 issued May 8, 2001, which is a Continuation-in-Part of copending International Application PCT/FR97/01316, having an international filing date of Jul. 15, 1997 and designating the U.S. and claiming priority from French Application No. 96/09401, filed Jul. 19, 1996, now French Patent No. 2751227B1 issued Nov. 27, 1998.

Each of the foregoing applications and patents, and each document cited or referenced in each of the foregoing applications and patents, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

BACKGROUND OF THE INVENTION

The present invention relates to a vaccine formula allowing the vaccination of dogs against a large number of infectious pathologies, in particular respiratory and digestive pathologies. It also relates to a corresponding method of vaccination.

Infectious dog pathology is extremely varied and often difficult to control depending on the circumstances encountered in the field.

A number of vaccines already exist, in particular against Carré's disease (CDV virus), parvovirosis (CPV virus), coronavirosis (CCV virus), kennel cough or respiratory complex (PI2 virus) and rabies (rhabdovirus). These vaccines are, more generally, live vaccines consisting of attenuated strains. This is especially the case for Carré's disease vaccines, vaccines against canine adenoviroses, vaccines against parvovirosis and vaccines against the canine coronavirus.

In some cases, inactivated vaccines have also been proposed, as for rabies and coronavirosis.

These various vaccines are sold either separately, that is to say in the form of monovalent vaccines, or in the form of associated, that is to say polyvalent, vaccines.

The polyvalent associations developed up until now have always posed problems of compatibility between the valencies and of stability. It is indeed necessary to ensure at the same time the compatibility between the different valencies of the vaccine, whether from the point of view of the different antigens used or from the point of view of the formulations themselves, especially in the case where both inactivated vaccines and live vaccines are combined. It also poses the problem of preservation of such combined vaccines and also of their safety especially in the presence of adjuvant. These vaccines are in general quite expensive.

The degree of protection and the duration of this protection can, in addition, be highly variable and are also sensitive to the circumstances in the field. This is particularly true of the vaccination of puppies, in which the antibodies of maternal origin prevent immunization by the inactivated vaccines and even by live vaccines.

It may therefore be desirable to perfect the vaccination of Canidae, and especially dogs, while keeping in mind the economic constraints acting against the use of vaccines which are expensive or complicated to use.

Vaccination trials against Carré's disease using purified preparations of F fusion antigens and of H haemaglutinin equivalents in complete Freund's adjuvant have suggested that the F antigen might constitute an immunogen of interest for protection against the CDV virus (E. Norrby et al., J. of Virol. May 1986: 536-541) for a subunit vaccine.

Another article (P. de Vries et al., J. gen. Virol. 1988, 69: 2071-2083) suggests, on the other hand, that the CDV F and HA proteins might be advantageous in a vaccination according to the technique of immunostimulatory complexes (IS-COMS).

Mice immunized with a recombinant vaccine expressing the gene for the CDV F protein were protected against challenge with this virus.

These are, however, laboratory results, which are difficult to interpret especially under field conditions.

As regards parvoviroses, trials of subunit vaccines containing the major capsid protein VP2 from the CPV virus obtained by genetic recombination in the baculovirus made it possible to show protection of dogs thus immunized against challenge with the CPV virus.

As regards the canine herpesvirus CHV, studies have been carried out on the use of glycoproteins as components of subunit vaccines. These studies have shown the induction of cross-responses with other herpesviruses such as FHV but do not draw any conclusion on the possibilities of making a protective vaccine.

For the Lyme disease, associated OspA and OspB induce protection in mice and dogs and OspA alone in mice, hamsters and dogs.

Patent applications WO-A-90 11092, WO-A-93 19183, WO-A-94 21797 and WO-A-95 20660 have made use of the recently developed technique of polynucleotide vaccines. It is known that these vaccines use a plasmid capable of expressing, in the host cells, the antigen inserted into the plasmid. All routes of administration have been proposed (intraperitoneal, intravenous, intramuscular, transcutaneous, intradermal, mucosal and the like). Various means of vaccination can also be used, such as DNA deposited at the surface of gold particles and projected so as to penetrate into the animal's skin (Tang et al., Nature 356, 152-154, 1992) and liquid jet injectors which make it possible to transfect the skin, muscle, fatty tissues as well as the mammary tissues (Furth et al., Analytical Biochemistry, 205, 365-368, 1992).

The polynucleotide vaccines may use both naked DNAs and DNAs formulated, for example, inside liposomes or cationic lipids.

The prior art, on the other hand, gives no result of protection in dogs by the polynucleotide method of vaccination against these diseases. Much less is yet known about the canine coronavirus CCV and about the agents responsible for the respiratory complex.

As regards rabies, protection of mice against virulent challenge has been demonstrated after treatment with a polynucleotide vaccine expressing the gene for the G protein under the control of the SV40 virus early promoter (Xiang et al., Virology 199, 1994: 132-140), a similar result being achieved by using the CMV IE promoter.

OBJECT OF THE INVENTION

The invention proposes to provide a multivalent vaccine formula which makes it possible to ensure vaccination of dogs against a number of pathogenic agents.

Another objective of the invention is to provide such a vaccine formula combining different valencies while exhibiting all the required criteria of mutual compatibility and stability of the valencies.

Another objective of the invention is to provide such a vaccine formula which makes it possible to combine different valencies in the same vehicle.

Another objective of the invention is to provide such a vaccine formula which is easy and inexpensive to use.

Yet another objective of the invention is to provide a method of vaccination which makes it possible to considerably increase the efficacy of the vaccine according to the invention or to substantially reduce the quantity of vaccine necessary, and having good safety.

Still another objective of the invention is the induction in a Canidae host of long-term (e.g. more than 6 months, preferably more than 1 year, more preferably more than 416 days) immunity, preferably long-term protective immunity, against rabies, by administering a vaccine containing a plasmid comprising and expressing in vivo the rabies G gene, and/or the rapid induction ("short-term", e.g. in a couple of days, preferably at least one week, more preferably at least two weeks after vaccine administration) in a Canidae host of immunity, preferably protective immunity, and more preferably rapidly established long-term protective immunity, against rabies by administering a vaccine containing a plasmid comprising and expressing in vivo the rabies G gene, and/or the induction in a Canidae host such a long-term and/or short-term immunity (as herein described above), preferably protective immunity, against rabies, by administering only once ("one shot") a vaccine containing a plasmid comprising and expressing in vivo the rabies G gene.

BRIEF DESCRIPTION OF THE DRAWINGS

FIG. 1 Plasmid pVR1012
FIG. 2 Plasmid pAB044
FIG. 3 Plasmid pAB036
FIG. 4 Plasmid pAB024
FIG. 5 Plasmid pAB021
FIG. 6 Plasmid pAB022
FIG. 7 Plasmid pAB037
FIG. 8 Plasmid pAB038
FIG. 9 Plasmid pAB017
FIG. 10 Plasmid pAB041

DETAILED DESCRIPTION

The subject of the present invention is therefore a vaccine formula against Canidae pathogens, comprising at least two vaccine valencies each comprising a plasmid integrating, so as to express it in vivo in the Canidae cells, a gene with one canine pathogen valency, namely a Carré's disease virus CDV valency and a canine parvovirus CPV valency, the plasmids comprising, for each valency, one or more of the genes selected from the group consisting of HA and F for the Carré's disease virus and the VP2 gene for the canine parvovirus.

Preferably, for the Carré's disease valency, the plasmid(s) comprise the HA and F genes, either inserted into the same plasmid, or inserted into different plasmids.

The multivalent vaccine according to the invention may also comprise a canine coronavirus CCV valency, with one or several plasmids comprising one or more of the genes selected from the group of the S and M genes and preferably the S gene or the S and M genes. Here also, the genes may be inserted into different plasmids or grouped together in the same plasmid in a context allowing their expression. The abovementioned bi- or trivalent vaccine according to the invention may also comprise, in addition, a valency effective for the prevention of the respiratory complex, namely a PI2 valency comprising one or several plasmids which comprise at least one of the HA and F genes. Preferably, the use of both the two HA and F genes is envisaged.

Other advantageous valencies in the case of the present invention may therefore be associated with the vaccines according to the invention, namely one or more of the valencies selected from the group formed by the herpesvirosis CHV, Lyme disease and rabies, the plasmids comprising, for each valency, one or more of the genes selected from the group composed of the gB and gD genes for the CHV virus, the OspA, OspB and p100 genes for B. burgdorferi (Lyme disease), and the G gene for rabies.

Preferably, for herpesvirosis, the two gB and gD genes are associated either in two separate plasmids, or in a single plasmid. For Lyme disease, the OspA gene is preferred.

Preferably, the vaccine according to the invention comprising the Carré's disease and parvovirosis valencies will comprise, as other valency, the coronavirosis valency or, less preferably, the respiratory complex valency, or these two valencies, it being understood that any combination comprising, one, several or all the coronavirosis, respiratory complex, herpesvirosis, Lyme disease and rabies valencies can be associated with the two Carré's disease and parvovirosis valencies.

Valency in the present invention is understood to mean at least one antigen providing protection against the virus for the pathogen considered, it being possible for the valency to contain, as subvalency, one or more modified or natural genes from one or more strains of the pathogen considered.

Pathogenic agent gene is understood to mean not only the complete gene but also the various nucleotide sequences, including fragments which retain the capacity to induce a protective response. The notion of the gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

The different valencies are contained in the vaccinal formulation according to the invention in a therapeutically effective quantity.

Preferably, the vaccine formula according to the invention can be provided in a suitable vehicle for administration, preferably by the intramuscular route, in a dose volume of between 0.1 and 5 ml, preferably between 0.2 and 2 ml, and more preferably between 0.25 and 1 ml.

The dose will be generally between 10 ng and 1 mg, preferably between 100 ng and 500 µg, preferably between 1 µg and 250 µg, and more preferably between 25 µg and 200 µg per plasmid type.

Use will preferably be made of naked plasmids simply placed in the vaccination vehicle which will be in general physiological saline (0.9% NaCl), ultrapure water, TE buffer and the like. All the polynucleotide vaccine forms described in the prior art can of course be used.

Each plasmid comprises a promoter capable of ensuring the expression of the gene inserted, under its control, into the host cells. This will be in general a strong eukaryotic promoter and in particular a cytomega-lovirus early CMV-IE promoter of human or murine origin, or optionally of another origin such as rats, pigs and guinea pigs.

More generally, the promoter may be either of viral origin or of cellular origin. As viral promoter other than CMV-IE, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, such as for example the desmin promoter (Bolmont et al., Journal of Submicroscopic Cytology and Pathology, 1990, 22, 117-122; and Zhenlin et al., Gene, 1989, 78, 243-254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen(s) of each valency, but it is also possible to envisage causing antigens of several valencies to be expressed by the same plasmid.

The subject of the present invention is also a method for vaccinating dogs, comprising the administration of an effective dose of a vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered in the context of this method of vaccination, by the different routes of administration proposed in the prior art in the case of polynucleotide vaccination and by means of known techniques of administration, the preferred route being the intramuscular route.

In one embodiment, administration is by subcutaneous, intradermal or intramuscular injection by the use of a needleless injector (e.g. Biojector™ or Vitajet™, Bioject Inc., Portland, Oreg., USA). With a needleless injector the dose of plasmid is between 10 ng and 1 mg, preferably between 100 ng and 500 µg, preferably from 1 µg to 250 µg, and more preferably between 25 µg and 200 µg per per plasmid. The volume of a dose can be comprised between 0.1 ml and 1.0 ml, preferably between 0.25 ml and 0.50 ml.

Administration can be done with a sole point of injection or with multiple points of injection. See also U.S. Ser. No. 09/232,469 as this apparatus can be as therein discussed.

The efficiency of presentation of the antigens to the immune system varies according to the tissues. In particular, the mucous membranes of the respiratory tree serve as barrier to the entry of pathogens and are associated with lymphoid tissues which support local immunity. The administration of a vaccine by contact with the mucous membranes, in particular the buccal mucous membrane, the pharyngeal mucous membrane and the mucous membrane of the bronchial region, is certainly of interest for vaccination against respiratory and digestive pathologies.

Consequently, the mucosal routes of administration form part of a mode of administration for the invention using in particular nebulization or spray or drinking water. It will be possible to apply the vaccine formulae and the vaccination methods according to the invention in this content.

The subject of the invention is also monovalent vaccine formulae comprising one or more plasmids encoding one or more genes from one of the viruses above, the genes being those described above. Besides their monovalent character, these formulae may possess the characteristics stated above as regards the choice of the genes, their combinations, the composition of the plasmids, the dose volumes, the doses and the like.

The monovalent vaccine formulae may be used (i) for the preparation of a polyvalent vaccine formula as described above, (ii) individually against the actual pathology, (iii) combined with a vaccine of another type (live or inactivated whole, recombinant, subunit) against another pathology, or (iv) as booster for a vaccine as described below.

The subject of the present invention is in fact also the use of one or more plasmids according to the invention for the manufacture of a canine vaccine intended to vaccinate animals first vaccinated by means of a first conventional vaccine (monovalent or multivalent) of the type in the prior art, in particular selected from the group consisting of a live whole vaccine, an inactivated whole vaccine, a subunit vaccine, a recombinant vaccine, this first vaccine having (that is to say containing or capable of expressing) the antigen(s) encoded by the plasmid(s) or antigen(s) providing cross-protection.

Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also the method of vaccination consisting in making a first vaccination as described above and a booster with a vaccine formula according to the invention.

In a preferred embodiment of the process according to the invention, there is administered in a first instance, to the animal, an effective dose of the vaccine of the conventional, especially inactivated, live, attenuated or recombinant type, or alternatively a subunit vaccine, so as to provide a first vaccination, and, after a period preferably of 2 to 6 weeks, the polyvalent or monovalent vaccine according to the invention is administered.

The subject of the invention is also a vaccination kit grouping together a first-vaccination vaccine as described above and a vaccine formula according to the invention for the booster. It also relates to a vaccine formula according to the invention accompanied by a leaflet indicating the use of this formula as a booster for a first vaccination as described above.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

| Sequence listing SEQ ID No. | |
|---|---|
| SEQ ID No. 1: | Oligonucleotide AB017 |
| SEQ ID No. 2: | Oligonucleotide AB018 |
| SEQ ID No. 3: | Oligonucleotide AB085 |
| SEQ ID No. 4: | Oligonucleotide AB086 |
| SEQ ID No. 5: | Oligonucleotide AB053 |
| SEQ ID No. 6: | Oligonucleotide AB054 |
| SEQ ID No. 7: | Oligonucleotide AB045 |
| SEQ ID No. 8: | Oligonucleotide AB048 |
| SEQ ID No. 9: | Oligonucleotide AB049 |
| SEQ ID No. 10: | Oligonucleotide AB050 |
| SEQ ID No. 11: | Oligonucleotide AB087 |
| SEQ ID No. 12: | Oligonucleotide AB088 |
| SEQ ID No. 13: | Oligonucleotide AB089 |
| SEQ ID No. 14: | Oligonucleotide AB090 |
| SEQ ID No. 15: | Oligonucleotide AB038 |
| SEQ ID No. 16: | Oligonucleotide AB039 |
| SEQ ID No. 17: | Oligonucleotide AB011 |
| SEQ ID No. 18: | Oligonucleotide AB012 |

EXAMPLES

Example 1

Culture of the Viruses

The viruses are cultured on the appropriate cellular system until a cytopathic effect is obtained. The cellular systems to be used for each virus are well known to persons skilled in the art. Briefly, cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

Example 2

Culture of the Bacteria

The *Borrelia burgdorferi* strains are cultured in appropriate media and according to conditions well known to persons skilled in the art. These conditions and media are in particular described by A. Barbour (J. Biol. Med. 1984, 57, 71-75). The extraction of the bacterial DNA was carried out according to the conditions described by W. Simpson et al. (Infect. Immun. 1990, 58, 847-853). The usual techniques described by J. Sambrook et al. (Molecular Cloning: A Laboratory Manual, 2nd Edition, Cold Spring Harbor Laboratory, Cold Spring Harbor, N.Y., 1989) can also be used.

Example 3

Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 ug/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultrapure water. It can then be digested with restriction enzymes.

Example 4

Isolation of the Viral Genomic RNAs

The RNA viruses were purified according to techniques well known to persons skilled in the art. The genomic viral RNA of each virus was then isolated using the "guanidium thiocyanate/phenol-chloroform" extraction technique described by P. Chomczynski and N. Sacchi (Anal. Biochem., 1987, 162, 156-159).

Example 5

Molecular Biology Techniques

All the constructions of plasmids were carried out using the standard molecular biology techniques described by J. Sambrook et al. (*Molecular Cloning: A Laboratory Manual*, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 6

RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (Sambrook J. et: al., 1989). Each RT-PCR reaction was performed with a pair of specific amplimers and taking, as template, the viral genomic RNA extracted. The complementary DNA ampli-

Example 7

Plasmid pVR1012

The plasmid pVR1012 (FIG. 1) was obtained from Vical Inc., San Diego, Calif., USA. Its construction has been described in J. Hartikka et al. (Human Gene Therapy, 1996, 7, 1205-1217).

Example 8

Construction of the Plasmid pAB044 (CDV HA Gene)

An RT-PCR reaction according to the technique of Example 6 was carried out with the Carré's disease virus (CDV) (Onderstepoort strain) genomic RNA (M. Sidhu et al., Virology, 1993, 193, 66-72), prepared according to the technique of Example 4, and with the following oligonucleotides:

AB017 (35 mer) (SEQ ID No. 1)
5'    AAAACTGCAGAATGCTCCCCTACCAAGA-CAAGGTG 3'
AB018 (37 mer) (SEQ ID No. 2)
5'    CGCGGATCCTTAACGGTTACAT-GAGAATCTTATACGG 3' so as to isolate the gene encoding the CDV HA glycoprotein in the form of a PstI-BamHI fragment. After purification, the 1835 by RT-PCR product was digested with PstI and BamHI in order to isolate a 1817 by PstI-BamHI fragment. This fragment was ligated with the vector pVR1012 (Example 7) previously digested with PstI and BamHI, to give the plasmid pAB044 (6676 bp) (FIG. 2).

Example 9

Construction of the Plasmid pAB036 (CDV F Gene)

An RT-PCR reaction according to the technique of Example 6 was carried out with the Carré's disease virus (CDV) (Onderstepoort strain) genomic RNA (R. Driellen, Genbank sequence accession No. X65509), prepared according to the technique of Example 4, and with the following oligonucleotides:

AB085 (40 mer) (SEQ ID No. 3)
5'    ATAAGAAGCGGCCGCACATGCACAAGG-GAATCCCCAAAAG 3'
AB086 (32 mer) (SEQ ID No. 4)
5' CGCGGATCCACTTCAGTGTGATCTCACATAGG 3' so as to isolate the gene encoding the CDV F glycoprotein in the form of an NotI-BamHI fragment. After purification, the 2018 bp RT-PCR product was digested with NotI and BamHI in order to isolate a 2000 by NotI-BamHI fragment. This fragment was ligated with the vector pVR1012 (Example 7), previously digested with NotI and BamHI, to give the plasmid pAB036 (6893 bp) (FIG. 3).

Example 10

Construction of the Plasmid pAB024 (Canine Parvovirus VP2 Gene)

A PCR reaction was carried out with the canine parvovirus (CPV) (CPV-b strain) genomic DNA (C. Parrish Genbank sequence accession No. M19296), prepared according to the technique of Example 3, and with the following oligonucleotides:

AB053 (33 mer) (SEQ ID No. 5)
5'   ACGCGTCGACATGAGTGATGGAGCAGTTCAACC 3'
AB054 (33 mer) (SEQ ID No. 6)
5' CGCGGATCCTTAATATAATTTTCTAGGTGCTAG 3' so as isolate the gene encoding the VP2 capsid protein (CPV VP2) in the form of a SalI-BamHI fragment. After purification, the 1773 bp PCR product was digested with SalI and BamHI in order to isolate a 1760 by SalI-BamHI fragment. This fragment was ligated with the vector pVR1012 (Example 7), previously digested with SalI and BamHI, to give the plasmid pAB024 (6629 bp) (FIG. 4).

Example 11

Construction of the Plasmid pAB021 (CCV S Gene)

An RT-PCR reaction according to the technique of Example 6 was carried out with the canine coronavirus (CCV) genomic RNA (B. Horsburgh et al., J. Gen. Virol. 1992, 73, 2849-2862), prepared according to the technique of Example 4, and, with the following oligonucleotides:

AB045 (32 mer) (SEQ ID No. 7)
5' ACGCGTCGACATGATTGTGCTTACATTGTGCC 3'
AB048 (35 mer) (SEQ ID No. 8)
5'CGCGGATCCTCAGTGAACATGAACTTTTTCAATAG 3' so as to amplify a 4374 by fragment containing the gene encoding the CCV S glycoprotein in the form of a SalI-BamHI fragment. After purification, the RT-PCR product was digested with SalI and BamHI to give a 4361 bp SalI-BamHI fragment. This fragment was ligated with the vector pVR1012 (Example 7), previously digested with SalI and BamHI to give the plasmid pAB021 (9230 bp) (FIG. 5).

Example 12

Construction of the Plasmid pAB022 (CCV M Gene)

An RT-PCR reaction according to the technique of Example 6 was carried out with the canine coronavirus (CCV) genomic RNA (B. Horsburgh et al., J. Gen. Virol. 1992, 73, 2849-2862), prepared according to the technique of Example 4,. and with the following oligonucleotides:

AB049 (34 mer) (SEQ. ID No. 9)
5' AAAACTGCAGAAATGAAGAAAATTTTGTTTTTAC 3'
AB050 (33 mer) (SEQ ID No. 10)
5'CGCGGATCCTTATACCATATGTAATAATTTTTC 3' so as to isolate the gene encoding the M glycoprotein (CCV M) in the form of a PstI-BamHI fragment. After purification, the 809 by RT-PCR product was digested with PstI and BamHI in order to isolate a 792 by PstI-BamHI fragment.

This fragment was ligated with the vector pVR1012 (Example 7), previously digested with PstI and BamHI, to give the plasmid pAB022 (5651 bp) (FIG. 6).

Example 13

Construction of the Plasmid pAB037 (CHV gB Gene)

A PCR reaction was carried out with the canine herpesvirus (CHV) (Carmichael strain) genomic DNA (K. Limbach et al., J. Gen. Virol. 1994, 75, 2029-2039), prepared according to the technique of Example 3, and with the following oligonucleotides:
AB087 (34 mer) (SEQ ID No. 11)
5' AAAACTGCAGAAGTATGTTTTCATTGTATCTATA 3'
AB088 (34 mer) (SEQ ID No. 12)
5'CTAGTCTAGATTATTAAACTTTACTTTCATTTTC 3' so as to isolate the gene encoding the CHV virus gB glycoprotein in the form of a PstI-XbaI fragment. After purification, the 2667 bp PCR product was digested with PstI and XbaI in order to isolate a 2648 bp PstI-XbaI fragment. This fragment was ligated with the vector pVR1012 (Example 7), previously digested with PstI-XbaI, to give the plasmid pAB037 (7523 bp) (FIG. 7).

Example 14

Construction of the Plasmid pAB038 (CHV gD Gene)

A PCR reaction was carried out with the canine herpesvirus (CHV) (Carmichael strain) genomic DNA (K. Limbach et al., J. Gen. Virol. 1994, 75, 2029-2039), prepared according to the technique of Example 3, and with the following oligonucleotides:
AB089 (34 mer) (SEQ ID No. 13)
5' AAACTGCAGAAAATGATTAAACTTCTATTTATC 3'
AB090 (35 mer) (SEQ ID No. 14)
5' ATAAGAATGCGGCCGCAAAGGCTAAACATTTGTTG 3' so as to isolate the gene encoding the CHV virus gD glycoprotein in the form of a PstI-NotI fragment. After purification, the 1072 bp PCR product was digested with PstI and NotI in order to isolate a 1049 by PstI-NotI fragment. This fragment was ligated with the vector pVR1012 (Example 7), previously digested with PstI and NotI, to give the plasmid pAB038 (5930 bp) (FIG. 8).

Example 15

Construction of the Plasmid pAB017 (*Borrelia burgdorferi* ospA Gene)

A PCR reaction was carried out with the Borrelia burgdorferi (B31 strain) genomic DNA (S. Bergstrom et al., Mol. Microbiol. 1989, 3, 479-486), prepared according to the technique of Example 2, and with the following olignnucleotides:
AB038 (37 mer) (SEQ ID No. 15)
5' ACGCGTCGACTATGAAAAAATATTTATTGGGAATAGG 3'
AB039 (34 mer) (SEQ ID No. 16)
5'CGCGGATCCCTTATTTTAAAGCGTTTTTAATTTC 3' so as to isolate the gene encoding the OspA membrane protein in the form of a SalI-BamHI fragment. After purification, the 842 bp PCR product was digested with SalI and BamHI in order to isolate an 829 by SalI-BamHI fragment. This fragment was ligated with the vector pVR1012 (Example 7), previously digested with SalI and BamHI, to give the plasmid pAB017 (5698 bp) (FIG. 9).

Example 16

Construction of the Plasmid pAB041 (Rabies Virus G Gene)

An RT-PCR reaction according to the technique of Example 6 was carried out with the rabies virus (ERA strain) genomic RNA (A. Anilionis et al., Nature, 1981, 294, 275-278), prepared according to the technique of Example 4, and with the following oligonucleotides:
AB011 (33 mer) (SEQ ID No. 17)
5' AAAACTGCAGAGATGGTTCCTCAGGCTCTCCTG 3'
AB012 (34 mer) (SEQ ID No. 18)
5'CGCGGATCCTCACAGTCTGGTCTCACCCCCACTC 3' so as to amplify a 1589 by fragment containing the gene encoding the rabies virus G glycoprotein. After purification, the RT-PCR product was digested with PstI and BamHI to give a 1578 by PstI-BamHI fragment. This fragment was ligated with the vector pVR1012 (Example 7), previously digested with PstI and BamHI, to give the plasmid pAB041 (6437 bp) (FIG. 10).

Example 17

Production and Purification of the Plasmids

For the preparation of the plasmids intended for the vaccination of animals, any technique may be used which makes it possible to obtain a suspension of purified plasmids predominantly in the supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (Molecular Cloning: A Laboratory Manual, 2nd edition, Cold Spring Harbor Laboratory, Cold Spring Harbor, N.Y., 1989). Reference may also be made to patent applications PCT WO 95/21250 and PCT WO 96/02658 which describe methods for producing, on an industrial scale, plasmids which can be used for vaccination. For the purposes of the manufacture of vaccines (see Example 18), the purified plasmids are resuspended so as to obtain solutions at a high concentration (>2 mg/ml) which are compatible with storage. To do this the plasmids are resuspended either in ultrapure water or in TE buffer (10 mM Tris-HC1; 1 mM EDTA, pH 8.0).

Example 18

Manufacture of the Associated Vaccines

The various plasmids necessary for the manufacture of an associated vaccine are mixed starting with their concentrated solutions (Example 16). The mixtures are prepared such that the final concentration of each plasmid corresponds to the effective dose of each plasmid. The solutions which can be used to adjust the final concentration of the vaccine may be either a 0.9% NaCl solution, or PBS buffer.

Specific formulations, such as liposomes and cationic lipids, may also be used for the manufacture of the vaccines.

Example 19

Vaccination of Dogs

The dogs are vaccinated with doses of 10 μg, 50 μg or 250 μg of plasmid.

The injections can be performed with a needle by the intramuscular route. In this case, the vaccinal doses are administered in volumes of 1 or 2 ml. The injections may be performed with a needle by the intradermal route. In this case, the vaccinal doses are administered in a total volume of 1 ml administered at 10 points of 0.1 ml or at: 20 points of 0.05 ml. The intradermal injections are performed after shaving the skin (thoracic flank in general) or at the level of a relatively glabrous anatomical region, for example the inner surface of the thigh. A liquid jet injection apparatus can also be used for the intradermal injections.

Example 20

Short Term Protection of Vaccinated Dogs

Two groups of five dogs each (conventional dogs, approximately 8 to 9 weeks old) were given intramuscular (IM) injections on day 0 of 0.25 ml of physiological solution (NaCl 0.9% in water) or of 0.25 ml of physiological solution containing 0.05 mg of plasmid pAB041 (see Example 16).

On day 14, both groups were challenged by intramuscular injection to the crotaphyte muscle (temporalis muscle) of 1.0 ml containing 3.8 log 10 LD50 of rabies virus strain New York (NY1042.90, available from the CDC, Laurenceville, USA).

Protection was illustrated by 100% protection (mortality of 0/5) in the vaccinated group. Conversely, there was 100% mortality (mortality of 5/5) in the control group.

These results demonstrate a protective immunity achieved through vaccination with a plasmid vaccine expressing the rabies G gene, and show that this protective immunity is present at two weeks post-vaccination.

Example 21

Long Term Protection of Vaccinated Dogs

Two groups of dogs (n=5 in vaccinated group, n=2 in control group) were given intramuscular injections on day 0 with 1.0 ml of physiological solution (as defined in Example 20) or 1.0 ml of physiological solution containing 0.2 mg of plasmid pAB041 (see Example 16 and 20). The dogs were approximately 20-24 weeks old at the time of the intramuscular injection, and were specific pathogen-free (SPF).

On day 416, both groups were challenged by intramuscular injection to the crotaphyte muscle (temporalis muscle) of 1.0 ml containing 3.8 log 10 LD50 of rabies virus strain New York (NY1042.90, available from the CDC, Laurenceville, USA).

Protection was illustrated by 100% protection (mortality of 0/5) in the vaccinated group. Conversely, there was 100% mortality (mortality of 2/2) in the control group.

Additionally, the change in anti-rabies antibodies was followed using the standard technique of rapid fluorescent focus inhibition test (RFFIT) from day 0 to day 168 (Smith, J. S. et al., in "Laboratory techniques in rabies", edited by Meslin, F. -X., Kaplan, M. M. and Koprowski, H., World Health Organization Geneva, 1996, 4$^{th}$ Ed., chapter 15, pages 181-192). Results (mean and standard deviation) are provided in the following table (log 10):

| | D0 | D14 | D28 | D42 | D56 | D84 | D112 | D140 | D168 |
|---|---|---|---|---|---|---|---|---|---|
| Mean | 0.5 | 1.6 | 1.6 | 1.6 | 1.5 | 1.5 | 1.3 | 1.6 | 1.4 |
| Standard deviation | 0.4 | 0.4 | 0.2 | 0.4 | 0.3 | 0.3 | 0.4 | 0.5 | 0.5 |

These results demonstrate a long-term protective immunity achieved through vaccination with a plasmid vaccine expressing the rabies G gene. Specifically, the vaccination has been shown to elicit an immunological response against Canidae pathogens, wherein the response is of at least one year in duration without the use of supplemental booster injections.

Example 22

Needleless Vaccination of Dogs

The RFFIT titer described in Example 21 was performed to asses the effectiveness of needleless vaccination of dogs.

5 dogs (12 to 13 weeks old) were injected using Biojector 2000 (Bioject Inc., Portland, Oreg., USA) with a number 5 chamber on day 0 with 0.50 ml of physiological solution containing 0.2 mg of plasmid pAB041 (Example 16, 20, and 21).

The results of the anti-rabies RFFIT titer (log 10) follows, as observed over days 0 to 84.

| | D0 | D14 | D28 | D56 | D84 |
|---|---|---|---|---|---|
| Mean | 0.8 | 1.6 | 1.7 | 2.0 | 1.8 |
| Standard deviation | 0.2 | 0.3 | 0.1 | 0.2 | 0.2 |

The results of the anti-rabies RFFIT titer were substantially identical to those obtained in Example 21, wherein the immunization was by intramuscular injection with a standard syringe and needle. This shows that needleless vaccination provides results that are equivalent to those obtained with traditional syringe and needle vaccinations.

Additionally, two group s of five dogs each (8 to 9 weeks old) were injected on day 0 with either 0.25 ml of physiological solution (See example 20) or 0.25 ml of physiological solution containing 0.05 mg of plasmid pAB041 (See example 16). The control group received the injection by traditional syringe and needle intramuscular injection. The vaccinated group received their injection using Vitajet™ (Bioject Inc., Portland, Oreg., USA) with the spring number 100 and the orifice of 0.07.

On day 14, both groups were challenged by intramuscular injection in the crotaphyte muscle (temporalis muscle) of 1.0 ml containing 3.8 log10 LD50 of rabies virus strain New York (NY1-42.90, available from the CDC, Laurenceville, USA).

Needleless injection of the vaccine provided protection in 80% of the group (mortality rate of 1/5). In the control group, there was a 100% mortality rate (mortality rate of 5/5).

Therefore, protective immunity is achieved using a needleless injector and a plasmid vaccine expressing rabies G gene, and that said immunity is present shortly after the injection.

We claim:

1. A method for vaccinating a Canidae comprising administering to said Canidae an effective amount of a vaccine comprising an effective amount of a plasmid that contains and expresses in a Canidae host cell a nucleic acid molecule having a nucleic acid sequence encoding rabies glycoprotein G, and a pharmaceutically acceptable carrier, wherein the vaccine provides complete protection against rabies for at least one year following a single administration of the vaccine.

2. The method according to claim 1, wherein the vaccine comprises from 10 ng to 1 mg of the plasmid.

3. The method according to claim 2, wherein the vaccine comprises from 100 ng to 500 μg of the plasmid.

4. The method according to claim 2, wherein the vaccine comprises between 1 μg and 250 μg of the plasmid.

5. The method according to claim 1, wherein the vaccine is administered by needleless injection.

6. A method for vaccinating a Canidae comprising administering to said Canidae an effective amount of a vaccine comprising 200 μg or less of a plasmid that contains and expresses in a Canidae host cell a nucleic acid molecule having a nucleic acid sequence encoding rabies glycoprotein G, and a pharmaceutically acceptable carrier, wherein the vaccine provides complete protection against rabies for at least one year.

7. The method according to claim 6, wherein the vaccine is administered by needleless injection.

8. The method according to claim 1 or claim 6, wherein expression of the nucleic acid sequence is under the control of a promoter selected from the group consisting of a CMV-IE promoter, a SV40 early promoter, a SV40 late promoter, a Rous sarcoma virus LTR promoter, and a promoter of a cytoskeleton gene.

9. The method according to claim 2, wherein the promoter is a CMV-IE promoter.

10. The method according to claim 1 or claim 6, wherein the vaccine is administered in a dose volume between 0.1 and 5 ml.

11. The method according to claim 10, wherein the vaccine is administered in a dose volume between 0.5 and 2 ml.

12. The method according to claim 5 or claim 7, wherein the vaccine is administered at 1-10 points on the animal.

13. The method according to claim 5 or claim 7, wherein the vaccine is administered at 4-6 points on the animal.

14. The method according to claim 5 or claim 7, wherein the vaccine is administered at 5 or 6 points on the animal.

15. The method according to claim 5 or claim 7, wherein the vaccine is administered at 5 points on the animal.

* * * * *

UNITED STATES PATENT AND TRADEMARK OFFICE
CERTIFICATE OF CORRECTION

PATENT NO. : 7,294,338 B2  Page 1 of 1
APPLICATION NO. : 10/211502
DATED : November 13, 2007
INVENTOR(S) : Jean-Christophe Audonnet, Annabelle Bouchardon and Michel Riviere It is certified that error appears in the above-identified patent and that said Letters Patent is hereby corrected as shown below:

On the Title Page:

Please insert

--Foreign Application Priority Data

French Application No. 96/09401; filed July 19, 1996--.

In the Claims:

Column 20, line 34, please correct "claim 2" to --claim 8--.

Signed and Sealed this

Twentieth Day of May, 2008

JON W. DUDAS
*Director of the United States Patent and Trademark Office*